(12) United States Patent
Zhang et al.

(10) Patent No.: US 8,436,014 B2
(45) Date of Patent: May 7, 2013

(54) SOLID FORMS OF N-(4-(7-AZABICYCLO[2.2.1]HEPTAN-7-YL)-2-(TRIFLUORORMETHYL)PHENYL)-4-OXO-5-(TRIFLUOROMETHYL)-1,4-DIHYROQUINOLINE-3-CARBOXAMIDE

(75) Inventors: Beili Zhang, San Diego, CA (US); Mariusz Krawiec, Marlborough, MA (US); Martyn Botfield, Concord, MA (US); Peter D. J. Grootenhuis, San Diego, CA (US); Fredrick Van Goor, San Diego, CA (US)

(73) Assignee: Vertex Pharmaceutical Incorporated, Cambridge, MA (US)

( * ) Notice: Subject to any disclaimer, the term of this patent is extended or adjusted under 35 U.S.C. 154(b) by 662 days.

(21) Appl. No.: 12/605,266

(22) Filed: Oct. 23, 2009

(65) Prior Publication Data

US 2010/0130547 A1    May 27, 2010

Related U.S. Application Data (60) Provisional application No. 61/107,813, filed on Oct. 23, 2008.

(51) Int. Cl.
*A61K 31/47* (2006.01)
*C07D 215/00* (2006.01)

(52) U.S. Cl.
USPC .......................................... 514/312; 546/156

(58) Field of Classification Search ................. 514/312; 546/156
See application file for complete search history.

(56) References Cited

U.S. PATENT DOCUMENTS
2011/0124869 A1 * 5/2011 Ambhaikar et al. .......... 546/156

FOREIGN PATENT DOCUMENTS
WO    2006/002421 A2    1/2006
WO    2007/079139 A2    7/2007

OTHER PUBLICATIONS
Brittain's publication, 1999, pp. 348-361.*
International Search Report of PCT/US2009/061942, dated Jan. 13, 2010.

* cited by examiner

*Primary Examiner* — Rei-tsang Shiao
(74) *Attorney, Agent, or Firm* — Honigman Miller Schwartz and Cohn LLP; Christopher C. Forbes; Jonathan P. O'Brien (57) ABSTRACT

The present invention relates to solid state forms, for example, crystalline forms of N-(4-(7-azabicyclo[2.2.1]heptan-7-yl)-2-(trifluoromethyl)phenyl)-4-oxo-5-(trifluoromethyl)-1,4-dihydroquinoline-3-carboxamide, pharmaceutical compositions thereof, and methods therewith.

13 Claims, 3 Drawing Sheets

SOLID FORMS OF N-(4-(7-AZABICYCLO[2.2.1]HEPTAN-7-YL)-2-(TRIFLUORORMETHYL)PHENYL)-4-OXO-5-(TRIFLUOROMETHYL)-1,4-DIHYDROQUINOLINE-3-CARBOXAMIDE

RELATED APPLICATIONS

This application claims the benefit of priority to U.S. Provisional Application Ser. No. 61/107,813, filed Oct. 23, 2008, entitled "SOLID FORMS OF N-(4-(7-AZABICYCLO[2.2.1]HEPTAN-7-YL)-2-(TRIFLUOROMETHYL)PHENYL)-4-OXO-5-(TRIFLUOROMETHYL)-1,4-DIHYDROQUINOLINE-3-CARBOXAMIDE", the entire contents of which is incorporated herein by reference.

TECHNICAL FIELD OF THE INVENTION

The present invention relates to solid state forms, for example, crystalline forms of N-(4-(7-azabicyclo[2.2.1]heptan-7-yl)-2-(trifluoromethyl)phenyl)-4-oxo-5-(trifluoromethyl)-1,4-dihydroquinoline-3-carboxamide, which is a modulator of cystic fibrosis transmembrane conductance regulator ("CFTR"). The invention also relates to pharmaceutical compositions including the crystalline forms of N-(4-(7-azabicyclo[2.2.1]heptan-7-yl)-2-(trifluoromethyl)phenyl)-4-oxo-5-(trifluoromethyl)-1,4-dihydroquinoline-3-carboxamide, and methods therewith.

BACKGROUND OF THE INVENTION

ATP cassette transporters are a family of membrane transporter proteins that regulate the transport of a wide variety of pharmacological agents, potentially toxic drugs, and xenobiotics, as well as anions. They are homologous membrane proteins that bind and use cellular adenosine triphosphate (ATP) for their specific activities. Some of these transporters were discovered as multidrug resistance proteins (like the MDR1-P glycoprotein, or the multidrug resistance protein, MRP1), defending malignant cancer cells against chemotherapeutic agents. To date, 48 such transporters have been identified and grouped into 7 families based on their sequence identity and function.

One member of the ATP cassette transporters family commonly associated with disease is the cAMP/ATP-mediated anion channel, CFTR. CFTR is expressed in a variety of cells types, including absorptive and secretory epithelia cells, where it regulates anion flux across the membrane, as well as the activity of other ion channels and proteins. In epithelial cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), Riordan, J. R. et al. (1989) Science 245:1066-1073). A defect in this gene causes mutations in CFTR resulting in cystic fibrosis ("CF"), the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia lead to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, more than 1000 disease causing mutations in the CF gene have been identified (http://www.genet.sickkids.on.ca/cftr/). The most prevalent mutation is a deletion of phenylalanine at position 508 of the CFTR amino acid sequence, and is commonly referred to as ΔF508-CFTR. This mutation occurs in approximately 70 percent of the cases of cystic fibrosis and is associated with a severe disease.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia, leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dolmans et al. (1991), Nature Lond. 354: 526-528; Denning et al., supra; Pasyk and Foskett (1995), J. Cell. Biochem. 270: 12347-50). In addition to ΔF508-CFTR, R117H-CFTR and G551D-CFTR, other disease causing mutations in CFTR that result in defective trafficking, synthesis, and/or channel gating, could be up- or down-regulated to alter anion secretion and modify disease progression and/or severity.

Although CFTR transports a variety of molecules in addition to anions, it is clear that this role (the transport of anions, chloride and bicarbonate) represents one element in an important mechanism of transporting ions and water across the epithelium. The other elements include the epithelial $Na^+$ channel, ENaC, $Na^+/2Cl^-/K^+$ co-transporter, $Na^+$—$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and Cl channels expressed on the basolateral surface of the cell. Secondary active transport of chloride from the luminal side leads to the accumulation of intracellular chloride, which can then passively leave the cell via Cl⁻ ion channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

Defective bicarbonate transport due to mutations in CFTR is hypothesized to cause defects in certain secretory functions. See, e.g., "Cystic fibrosis: impaired bicarbonate secretion and mucoviscidosis," Paul M. Quinton, Lancet 2008; 372: 415-417.

Mutations in CFTR that are associated with moderate CFTR dysfunction are also evident in patients with conditions that share certain disease manifestations with CF but do not meet the diagnostic criteria for CF. These include congenital bilateral absence of the vas deferens, idiopathic chronic pancreatitis, chronic bronchitis, and chronic rhinosinusitis. Other diseases in which mutant CFTR is believed to be a risk factor along with modifier genes or environmental factors include primary sclerosing cholangitis, allergic bronchopulmonary aspergillosis, and asthma.

Cigarette smoke, hypoxia, and environmental factors that induce hypoxic signaling have also been demonstrated to impair CFTR function and may contribute to certain forms of respiratory disease, such as chronic bronchitis. Diseases that may be due to defective CFTR function but do not meet the diagnostic criteria for CF are characterized as CFTR-related diseases.

In addition to cystic fibrosis, modulation of CFTR activity may be beneficial for other diseases not directly caused by mutations in CFTR, such as secretory diseases and other protein folding diseases mediated by CFTR. CFTR regulates chloride and bicarbonate flux across the epithelia of many cells to control fluid movement, protein solubilization, mucus viscosity, and enzyme activity. Defects in CFTR can cause blockage of the airway or ducts in many organs, including the liver and pancreas. Potentiators are compounds that enhance the gating activity of CFTR present in the cell membrane. Any disease which involves thickening of the mucus, impaired fluid regulation, impaired mucus clearance, or blocked ducts leading to inflammation and tissue destruction could be a candidate for potentiators.

These include, but are not limited to, chronic obstructive pulmonary disease (COPD), asthma, smoke induced COPD, chronic bronchitis, rhinosinusitis, constipation, dry eye disease, and Sjögren's Syndrome, gastro-esophageal reflux disease, gallstones, rectal prolapse, and inflammatory bowel disease. COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimized periciliary fluid viscosity. This would lead to enhanced mucociliary clearance and a reduction in the symptoms associated with COPD. In addition, by preventing ongoing infection and inflammation due to improved airway clearance, CFTR modulators may prevent or slow the parenchimal destruction of the airway that characterizes emphysema and reduce or reverse the increase in mucus secreting cell number and size that underlyses mucus hypersecretion in airway diseases. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as cystic fibrosis and Sjögrens's syndrome. Increasing anion secretion via CFTR would enhance fluid transport from the corneal endothelial cells and secretory glands surrounding the eye to increase corneal hydration. This would help to alleviate the symptoms associated with dry eye disease. Sjögrens's syndrome is an autoimmune disease in which the immune system attacks moisture-producing glands throughout the body, including the eye, mouth, skin, respiratory tissue, liver, vagina, and gut. Symptoms, include, dry eye, mouth, and vagina, as well as lung disease. The disease is also associated with rheumatoid arthritis, systemic lupus, systemic sclerosis, and polymypositis/dermatomyositis. Defective protein trafficking is believed to cause the disease, for which treatment options are limited. Modulators of CFTR activity may hydrate the various organs afflicted by the disease and may help to alleviate the associated symptoms. Individuals with cystic fibrosis have recurrent episodes of intestinal obstruction and higher incidences of rectal polapse, gallstones, gastro-esophageal reflux disease, GI malignancies, and inflammatory bowel disease, indicating that CFTR function may play an important role in preventing such diseases.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of CFTR by the ER machinery, has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5(7), pp 745- 751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)]. The diseases associated with the first class of ER malfunction are cystic fibrosis (due to misfolded ΔF508-CFTR as discussed above), hereditary emphysema (due to al -antitrypsin; non Piz variants), hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, Mucopolysaccharidoses (due to lysosomal processing enzymes), Sandhof/Tay-Sachs (due to β-hexosaminidase), Crigler-Najjar type II (due to UDP-glucuronyl-sialyctransferase), polyendocrinopathy/hyperinsulemia, Diabetes mellitus (due to insulin receptor), Laron dwarfism (due to growth hormone receptor), myleoperoxidase deficiency, primary hypoparathyroidism (due to preproparathyroid hormone), melanoma (due to tyrosinase). The diseases associated with the latter class of ER malfunction are Glycanosis CDG type 1, hereditary emphysema (due to α1-Antitrypsin (PiZ variant), congenital hyperthyroidism, osteogenesis imperfecta (due to Type I, II, IV procollagen), hereditary hypofibrinogenemia (due to fibrinogen), ACT deficiency (due to α1-antichymotrypsin), Diabetes insipidus (DI), neurophyseal DI (due to vasopvessin hormone/V2-receptor), neprogenic DI (due to aquaporin Charcot-Marie Tooth syndrome (due to peripheral myelin protein 22), Perlizaeus-Merzbacher disease, neurodegenerative diseases such as Alzheimer's disease (due to βAPP and presenilins), Parkinson's disease, amyotrophic lateral sclerosis, progressive supranuclear palsy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease (due to lysosomal α-galactosidase A), Straussler-Scheinker syndrome (due to Prp processing defect), infertility pancreatitis, pancreatic insufficiency, osteoporosis, osteopenia, Gorham's Syndrome, chloride channelopathies, myotonia congenita (Thomson and Becker forms), Bartter's syndrome type III, Dent's disease, hyperekplexia, epilepsy, hyperekplexia, lysosomal storage disease, Angelman syndrome, Primary Ciliary Dyskinesia (PCD), PCD with situs inversus (also known as Kartagener syndrome), PCD without situs inversus and ciliary aplasia, and liver disease.

Other diseases implicated by a mutation in CFTR include male infertility caused by congenital bilateral absence of the vas deferens (CBAVD), mild pulmonary disease, idiopathic pancreatitis, and allergic bronchopulmonary aspergillosis (ABPA). See, "CFTR-opathies: disease phenotypes associated with cystic fibrosis transmembrane regulator gene mutations," Peader G. Noone and Michael R. Knowles, Respir. Res. 2001, 2: 328-332 (incorporated herein by reference).

In addition to up-regulation of CFTR activity, reducing anion secretion by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Although there are numerous causes of diarrhea, the major consequences of diarrheal diseases, resulting from excessive chloride transport are common to all, and include dehydration, acidosis, impaired growth and death. Acute and chronic diarrheas represent a major medical problem in many areas of the world. Diarrhea is both a significant factor in malnutrition and the leading cause of death (5,000,000 deaths/year) in children less than five years old.

Secretory diarrheas are also a dangerous condition in patients with acquired immunodeficiency syndrome (AIDS) and chronic inflammatory bowel disease (IBD). Sixteen million travelers to developing countries from industrialized nations every year develop diarrhea, with the severity and number of cases of diarrhea varying depending on the country and area of travel.

Accordingly, there is a need for potent and selective CFTR potentiators of wild-type and mutant forms of human CFTR. These mutant CFTR forms include, but are not limited to, ΔF508del, G551D, R117H, 2789+5G->A.

There is also a need for modulators of CFTR activity, and compositions thereof, which can be used to modulate the activity of the CFTR in the cell membrane of a mammal.

There is a need for methods of treating diseases caused by mutation in CFTR using such modulators of CHR activity.

There is a need for methods of modulating CFTR activity in an ex vivo cell membrane of a mammal.

In addition, there is a need for stable solid forms of said compound that can be used readily in pharmaceutical compositions suitable for use as therapeutics.

SUMMARY OF THE INVENTION

The present invention relates to solid forms of N-(4-(7-azabicyclo[2.2.1]heptan-7-yl)-2-(trifluoromethyl)phenyl)-4-oxo-5-(trifluoromethyl)-1,4-dihydroquinoline-3-carboxamide (hereinafter "Compound 1") which has the structure below:

Compound 1

Compound 1 and pharmaceutically acceptable compositions thereof are useful for treating or lessening the severity of a variety of diseases, disorders, or conditions, including, but not limited to, cystic fibrosis, pancreatitis, sinusitis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, Abetalipoproteinemia, lysosomal storage diseases, such as I-cell disease/pseudo-hurler, mucopolysaccharidoses, sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, Diabetes insipidus (DI), neurophyseal DI, neprogenic DI, Charcot-Marie tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease, Fabry disease, Straussler-Scheinker syndrome, COPD, dry-eye disease, pancreatic insufficiency, osteoporosis, osteopenia, Gorham's Syndrome, chloride channelopathies, myotonia congenita (Thomson and Becker forms), Bartter's syndrome type III, Dent's disease, hyperekplexia, epilepsy, hyperekplexia, lysosomal storage disease, Angelman syndrome, Primary Ciliary Dyskinesia (PCD), PCD with situs inversus (also known as Kartagener syndrome), PCD without situs inversus and ciliary aplasia, and Sjögren's disease.

In one aspect, Compound 1 is in a substantially crystalline, neat free form Form A.

Processes described herein can be used to prepare the compositions of this invention comprising Form A. The amounts and the features of the components used in the processes are be as described herein.

DETAILED DESCRIPTION OF THE INVENTION

Definitions

As used herein, the following definitions shall apply unless otherwise indicated.

The term "ABC-transporter" as used herein means an ABC-transporter protein or a fragment thereof comprising at least one binding domain, wherein said protein or fragment thereof is present in vivo or in vitro. The term "binding domain" as used herein means a domain on the ABC-transporter that can bind to a modulator. See, e.g., Hwang, T. C. et al., J. Gen. Physiol. (1998): 111(3), 477-90.

The term "CFTR" as used herein means cystic fibrosis transmembrane conductance regulator or a mutation thereof capable of regulator activity, including, but not limited to, ΔF508 CFTR, R117H CFTR, and G551D CFTR (see, e.g., http://www.genet.sickkids.on.ca/cftr/, for CFTR mutations).

The term "modulating" as used herein means increasing or decreasing by a measurable amount.

The term "normal CFTR" or "normal CFTR function" as used herein means wild-type like CFTR without any impairment due to environmental factors such as smoking, pollution, or anything that produces inflammation in the lungs.

The term "reduced CFTR" or "reduced CFTR function" as used herein means less than normal CFTR or less than normal CFTR function.

As used herein "crystalline" refers to compounds or compositions where the structural units are arranged in fixed geometric patterns or lattices, so that crystalline solids have rigid long range order. The structural units that constitute the crystal structure can be atoms, molecules, or ions. Crystalline solids show definite melting points.

As used herein the phrase "substantially crystalline", means a solid material that is arranged in fixed geometric patterns or lattices that have rigid long range order. For example, substantially crystalline materials have more than about 85% crystallinity (e.g., more than about 90% crystallinity or more than about 95% crystallinity). It is also noted that the term 'substantially crystalline' includes the descriptor 'crystalline', which is defined in the previous paragraph.

In one aspect, the invention features a form of N-(4-(7-azabicyclo[2.2.1]heptan-7-yl)-2-(trifluoromethyl)phenyl)-4-oxo-5-(trifluoromethyl)-1,4-dihydroquinoline-3-carboxamide characterized as Form A.

In some embodiments, Form A is characterized by one or more peaks: from about 7.7 to about 8.1 degrees, for example, about 7.9 degrees; from about 11.7 to about 12.1 degrees, for example, about 11.9 degrees; from about 14.2 to about 14.6 degrees, for example, about 14.4 degrees; and about 15.6 to about 16.0 degrees, for example, about 15.8 degrees; in an X-ray powder diffraction obtained using Cu K alpha radiation.

In some embodiments, Form A is characterized by one or more peaks: from about 7.8 to about 8.0 degrees, for example, about 7.9 degrees; from about 11.8 to about 12.0 degrees, for example, about 11.9 degrees; from about 14.3 to about 14.5 degrees, for example, about 14.4 degrees; and about 15.7 to about 15.9 degrees, for example, about 15.8 degrees; in an X-ray powder diffraction obtained using Cu K alpha radiation.

In other embodiments, Form A is characterized by one or more peaks from about: 7.7 to about 8.1 degrees, for example, about 7.9 degrees; from about 21.6 to about 22.0 degrees, for example, about 21.8 degrees; and about 23.6 to about 24.0 degrees, for example, about 23.8 degrees; in an X-ray powder diffraction obtained using Cu K alpha radiation.

In still other embodiments, Form A is characterized by one or more peaks from about: 7.8 to about 8.0 degrees, for example, about 7.9 degrees; from about 21.7 to about 21.9 degrees, for example, about 21.8 degrees; and about 23.7 to about 23.9 degrees, for example, about 23.8 degrees; in an X-ray powder diffraction obtained using Cu K alpha radiation.

In some embodiments, Form A is characterized by one or more of the following peaks measured in degrees in an X-ray powder diffraction pattern: a peak from about 7.7 to about 8.1 degrees (e.g., about 7.9 degrees); a peak from about 9.1 to about 9.5 degrees, (e.g., about 9.3 degrees); a peak from about 11.7 to about 12.1 degrees, (e.g., about 11.9 degrees); a peak from about 14.2 to about 14.6 degrees, (e.g., about 14.4 degrees); a peak from about 14.9 to about 15.3 degrees, (e.g., about 15.1 degrees); a peak from about 15.6 to about 16.0 degrees, (e.g., about 15.8 degrees); a peak from about 16.8 to about 17.2 degrees, (e.g., about 17.0 degrees); a peak from about 17.5 to about 17.9 degrees, (e.g., about 17.7 degrees); a peak from about 19.1 to about 19.5 degrees, (e.g., about 19.3 degrees); a peak from about 19.9 to about 20.3 degrees, (e.g., about 20.1 degrees); a peak from about 21.2 to about 21.6 degrees, (e.g., about 21.4 degrees); a peak from about 21.6 to about 22.0 degrees, (e.g., about 21.8 degrees); a peak from about 23.2 to about 23.6 degrees, (e.g., about 23.4 degrees); a peak from about 23.6 to about 24.0 degrees, (e.g., about 23.8 degrees); a peak from about 25.4 to about 25.8 degrees, (e.g., about 25.6 degrees); a peak from about 26.6 to about 27.0 degrees, (e.g., about 26.8 degrees); a peak from about 29.2 to about 29.6 degrees, (e.g., about 29.4 degrees); a peak from about 29.5 to about 29.9 degrees, (e.g., about 29.7 degrees); a peak from about 29.9 to about 30.3 degrees, (e.g., about 30.1 degrees); and a peak from about 31.0 to about 31.4 degrees, (e.g., about 31.2 degrees).

In some embodiments, Form A is characterized by one or more of the following peaks measured in degrees in an X-ray powder diffraction pattern: a peak from about 7.8 to about 8.0 degrees (e.g., about 7.9 degrees); a peak from about 9.2 to about 9.4 degrees, (e.g., about 9.3 degrees); a peak from about 11.8 to about 12.0 degrees, (e.g., about 11.9 degrees); a peak from about 14.3 to about 14.5 degrees, (e.g., about 14.4 degrees); a peak from about 15.0 to about 15.2 degrees, (e.g., about 15.1 degrees); a peak from about 15.7 to about 15.9 degrees, (e.g., about 15.8 degrees); a peak from about 16.9 to about 17.1 degrees, (e.g., about 17.0 degrees); a peak from about 17.6 to about 17.8 degrees, (e.g., about 17.7 degrees); a peak from about 19.2 to about 19.4 degrees, (e.g., about 19.3 degrees); a peak from about 20.0 to about 20.2 degrees, (e.g., about 20.1 degrees); a peak from about 21.3 to about 21.5 degrees, (e.g., about 21.4 degrees); a peak from about 21.7 to about 21.9 degrees, (e.g., about 21.8 degrees); a peak from about 23.3 to about 23.5 degrees, (e.g., about 23.4 degrees); a peak from about 23.7 to about 23.9 degrees, (e.g., about 23.8 degrees); a peak from about 25.5 to about 25.7 degrees, (e.g., about 25.6 degrees); a peak from about 26.7 to about 26.9 degrees, (e.g., about 26.8 degrees); a peak from about 29.3 to about 29.5 degrees, (e.g., about 29.4 degrees); a peak from about 29.6 to about 29.8 degrees, (e.g., about 29.7 degrees); a peak from about 30.0 to about 30.2 degrees, (e.g., about 30.1 degrees); and a peak from about 31.1 to about 31.3 degrees, (e.g., about 31.2 degrees).

Figure 1:
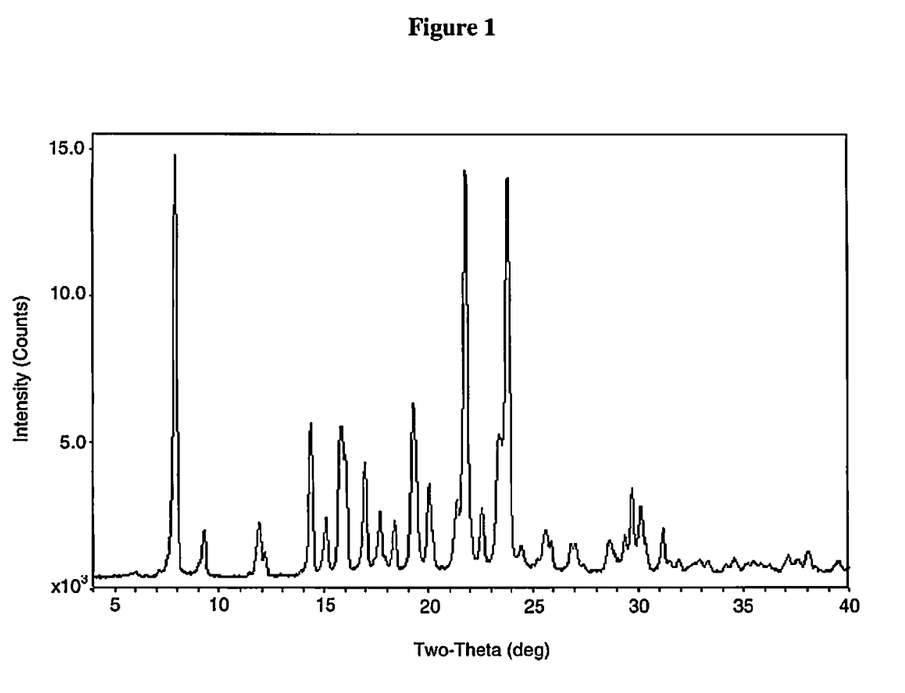
FIG. 1 is an X-ray powder diffraction pattern of Form A.

In some embodiments, Form A is characterized by a diffraction pattern as provided in FIG. 1.

In one aspect, the invention features a pharmaceutical composition comprising Form A and a pharmaceutically acceptable adjuvant or carrier.

In one aspect, the present invention features a method of treating a CFTR mediated disease in a human comprising administering to the human an effective amount of Form A.

In some embodiments, the method comprises administering an additional therapeutic agent.

In some embodiments, the disease is selected from cystic fibrosis, pancreatitis, sinusitis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease, Fabry disease, Straussler-Scheinker syndrome, COPD, dry-eye disease, pancreatic insufficiency, osteoporosis, osteopenia, Gorham's Syndrome, chloride channelopathies, myotonia congenita (Thomson and Becker forms), Bartter's syndrome type III, Dent's disease, hyperekplexia, epilepsy, hyperekplexia, lysosomal storage disease, Angelman syndrome, Primary Ciliary Dyskinesia (PCD), PCD with situs inversus (also known as Kartagener syndrome), PCD without situs inversus and ciliary aplasia, and Sjögren's disease.

In one embodiment, the present invention provides a method of treating cystic fibrosis in a human, comprising administering to said human an effective amount of Form A.

In one aspect, the present invention features a pharmaceutical pack or kit comprising Form A and a pharmaceutically acceptable carrier.

In one aspect, the invention features a crystal form of N-(4-(7-azabicyclo[2.2.1]heptan-7-yl)-2-(trifluoromethyl)phenyl)-4-oxo-5-(trifluoromethyl)-1,4-dihydroquinoline-3-carboxamide having a trigonal crystal system, a R-3 space group, and the following unit cell dimensions: a=19.1670(4) Å, b=19.1670(4) Å, c=33.6572(12) Å, α=90°, β=90°, and γ=120°.

In one embodiment, the present invention provides a crystal form of N-(4-(7-azabicyclo[2.2.1]heptan-7-yl)-2-(trifluoromethyl)phenyl)-4-oxo-5-(trifluoromethyl)-1,4-dihydroquinoline-3-carboxamide having unit cell dimensions: a=19.1670(4) Å, b=19.1670(4) Å, c=33.6572(12) Å.

Uses, Formulation and Administration

Pharmaceutically Acceptable Compositions

In one aspect of the present invention, pharmaceutically acceptable compositions are provided, wherein these compositions comprise Form A as described herein, and optionally comprise a pharmaceutically acceptable carrier, adjuvant or vehicle. In certain embodiments, these compositions optionally further comprise one or more additional therapeutic agents.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, the present invention provides a method of treating or lessening the severity of a condition, disease, or disorder implicated by CFTR mutation. In certain embodiments, the present invention provides a method of treating a condition, disease, or disorder implicated by a deficiency of the CFTR activity, the method comprising administering a composition comprising a compound 1 Form A to a subject, preferably a mammal, in need thereof.

In certain embodiments, the present invention provides a method of treating diseases associated with reduced CFTR function due to mutations in the gene encoding CFTR or environmental factors (e.g., smoke). These diseases include, cystic fibrosis, chronic bronchitis, recurrent bronchitis, acute bronchitis, male infertility caused by congenital bilateral absence of the vas deferens (CBAVD), female infertility caused by congenital absence of the uterus and vagina (CAUV), idiopathic chronic pancreatitis (ICP), idiopathic recurrent pancreatitis, idiopathic acute pancreatitis, chronic rhinosinusitis, primary sclerosing cholangitis, allergic bronchopulmonary aspergillosis, diabetes, dry eye, constipation, allergic bronchopulmonary aspergillosis (ABPA), bone diseases (e.g., osteoporosis), and asthma.

In certain embodiments, the present invention provides a method for treating diseases associated with normal CFTR function. These diseases include, chronic obstructive pulmonary disease (COPD), chronic bronchitis, recurrent bronchitis, acute bronchitis, rhinosinusitis, constipation, pancreatitis including chronic pancreatitis, recurrent pancreatitis, and acute pancreatitis, pancreatic insufficiency, male infertility caused by congenital bilateral absence of the vas deferens (CBAVD), mild pulmonary disease, idiopathic pancreatitis, liver disease, hereditary emphysema, gallstones, gasgtroesophageal reflux disease, gastrointestinal malignancies, inflammatory bowel disease, constipation, diabetes, arthritis, osteoporosis, and osteopenia.

In certain embodiments, the present invention provides a method for treating diseases associated with normal CFTR function including hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear palsy, Pick's disease, several polyglutarnine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, Gorham's Syndrome, chloride channelopathies, myotonia congenita (Thomson and Becker forms), Bartter's syndrome type III, Dent's disease, hyperekplexia, epilepsy, hyperekplexia, lysosomal storage disease, Angelman syndrome, Primary Ciliary Dyskinesia (PCD), PCD with situs inversus (also known as Kartagener syndrome), PCD without situs inversus and ciliary aplasia, or Sjogren's disease, comprising the step of administering to said mammal an effective amount of a composition comprising Form A described herein.

According to an alternative preferred embodiment, the present invention provides a method of treating cystic fibrosis comprising the step of administering to said mammal a composition comprising the step of administering to said mammal an effective amount of a composition comprising Form A described herein.

According to the invention an "effective amount" of Form A or a pharmaceutically acceptable composition thereof is that amount effective for treating or lessening the severity of one or more of the diseases, disorders or conditions as recited above.

Form A or a pharmaceutically acceptable composition thereof may be administered using any amount and any route of administration effective for treating or lessening the severity of one or more of the diseases, disorders or conditions as recited above.

In certain embodiments, Form A or a pharmaceutically acceptable composition thereof is useful for treating or lessening the severity of cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl⁻ concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, ΔF508.

In another embodiment, Form A described herein or a pharmaceutically acceptable composition thereof is useful for treating or lessening the severity of cystic fibrosis in patients who have residual CFTR activity induced or augmented using pharmacological methods or gene therapy. Such methods increase the amount of CFTR present at the cell surface, thereby inducing a hitherto absent CFTR activity in a patient or augmenting the existing level of residual CFTR activity in a patient.

In one embodiment, Form A described herein or a pharmaceutically acceptable composition thereof is useful for treating or lessening the severity of cystic fibrosis in patients within certain genotypes exhibiting residual CFTR activity, e.g., class III mutations (impaired regulation or gating), class IV mutations (altered conductance), or class V mutations (reduced synthesis) (Lee R. Choo-Kang, Pamela L., Zeitlin, *Type I, II, III, IV, and V cystic fibrosis Tansmembrane Conductance Regulator Defects and Opportunities of Therapy*; Current Opinion in Pulmonary Medicine 6:521-529, 2000). Other patient genotypes that exhibit residual CFTR activity include patients homozygous for one of these classes or heterozygous with any other class of mutations, including class I mutations, class II mutations, or a mutation that lacks classification.

In one embodiment, Form A described herein or a pharmaceutically acceptable composition thereof is useful for treating or lessening the severity of cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic insufficiency or patients diagnosed with idiopathic pancreatitis and congenital bilateral absence of the vas deferens, or mild lung disease.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, drops or patch), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 0.5 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline foini. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the Form A described herein or a pharmaceutically acceptable composition thereof can be employed in combination therapies, that is, Form A described herein or a pharmaceutically acceptable composition thereof can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated."

In one embodiment, the additional agent is selected from a mucolytic agent, bronchodialator, an anti-biotic, an anti-infective agent, an anti-inflammatory agent, a CFTR modulator other than a compound of the present invention, or a nutritional agent.

In one embodiment, the additional agent is an antibiotic. Exemplary antibiotics useful herein include tobramycin, including tobramycin inhaled powder (TIP), azithromycin, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In another embodiment, the additional agent is a mucolyte. Exemplary mucolytes useful herein includes Pulmozyme®.

In another embodiment, the additional agent is a bronchodialator. Exemplary bronchodialtors include albuterol, metaprotenerol sulfate, pirbuterol acetate, salmeterol, or tetrabuline sulfate.

In another embodiment, the additional agent is effective in restoring lung airway surface liquid. Such agents improve the movement of salt in and out of cells, allowing mucus in the lung airway to be more hydrated and, therefore, cleared more easily. Exemplary such agents include hypertonic saline, denufosol tetrasodium ([[[(3S, 5R)-5-(4-amino-2-oxopyrimidin-1-yl)-3-hydroxyoxolan-2-yl]methoxy-hydroxyphosphoryl] [[[(2R,3S,4R,5R)-5-(2,4-dioxopyrimidin-1-yl)-3,4-dihydroxyoxolan-2-yl]methoxy-hydroxyphosphoryl]oxy-hydroxyphosphoryl] hydrogen phosphate), or bronchitol (inhaled formulation of mannitol).

In another embodiment, the additional agent is an anti-inflammatory agent, i.e., an agent that can reduce the inflammation in the lungs. Exemplary such agents useful herein include ibuprofen, docosahexanoic acid (DHA), sildenafil, inhaled glutathione, pioglitazone, hydroxychloroquine, or simavastatin.

In another embodiment, the additional agent reduces the activity of the epithelial sodium channel blocker (ENaC) either directly by blocking the channel or indirectly by modulation of proteases that lead to an increase in ENaC activity (e.g., seine proteases, channel-activating proteases). Exemplary such agents include camostat (a trypsin-like protease inhibitor), QAU145, 552-02, GS-9411, INO-4995, Aerolytic, and amiloride. Additional agents that reduce the activity of the epithelial sodium channel blocker (ENaC) can be found, for example, in PCT Publication No. WO2009/074575, the entire contents of which are incorporated herein in their entirety.

Amongst other diseases described herein, combinations of CFTR modulators, such as Form A, and agents that reduce the activity of ENaC are use for treating Liddle's syndrome, an inflammatory or allergic condition including cystic fibrosis, primary ciliary dyskinesia, chronic bronchitis, chronic obstructive pulmonary disease, asthma, respiratory tract infections, lung carcinoma, xerostomia and keratoconjunctivitis sire, respiratory tract infections (acute and chronic; viral and bacterial) and lung carcinoma.

Combinations of CFTR modulators, such as Form A, and agents that reduce the activity of ENaC are also useful for treating diseases mediated by blockade of the epithelial sodium channel also include diseases other than respiratory diseases that are associated with abnormal fluid regulation across an epithelium, perhaps involving abnormal physiology of the protective surface liquids on their surface, e.g., xerostomia (dry mouth) or keratoconjunctivitis sire (dry eye). Furthermore, blockade of the epithelial sodium channel in the kidney could be used to promote diuresis and thereby induce a hypotensive effect.

Asthma includes both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g., of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".) Prophylactic efficacy in the treatment of asthma will be evidenced by reduced frequency or severity of symptomatic attack, e.g., of acute asthmatic or bronchoconstrictor attack, improvement in lung function or improved airways hyperreactivity. It may further be evidenced by reduced requirement for other, symptomatic therapy, i.e., therapy for or intended to restrict or abort symptomatic attack when it occurs, e.g., anti-inflammatory (e.g., cortico-steroid) or bronchodilatory. Prophylactic benefit in asthma may, in particular, be apparent in subjects prone to "morning dipping". "Morning dipping" is a recognized asthmatic syndrome, common to a substantial percentage of asthmatics and characterized by asthma attack, e.g., between the hours of about 4-6 am, i.e., at a time normally substantially distant from any previously administered symptomatic asthma therapy.

Chronic obstructive pulmonary disease includes chronic bronchitis or dyspnea associated therewith, emphysema, as well as exacerbation of airways hyperreactivity consequent to other drug therapy, in particular, other inhaled drug therapy. In some embodiments, the combinations of GPM modulators, such as Form A, and agents that reduce the activity of ENaC are useful for the treatment of bronchitis of whatever type or genesis including, e.g., acute, arachidic, catarrhal, croupus, chronic or phthinoid bronchitis.

In another embodiment, the additional agent is a CFTR modulator other than compound 1 Form A, i.e., an agent that has the effect of modulating CFTR activity. Exemplary such agents include ataluren ("PTC124®"; 3-[5-(2-fluorophenyl)-1,2,4-oxadiazol-3-yl]benzoic acid), sinapultide, lancovutide, depelestat (a human recombinant neutrophil elastase inhibitor), cobiprostone (7-{(2R,4aR,5R,7aR)-2-[(3S)-1,1-difluoro-3-methylpentyl]-2-hydroxy-6-oxooctahydrocyclopenta[b]pyran-5-yl}heptanoic acid), or (3-(6-(1-(2,2-difluorobenzo[d][1,3]dioxol-5-yl)cyclopropanecarboxamido)-3-methylpyridin-2-yl)benzoic acid. In another embodiment, the additional agent is (3-(6-(1-(2,2-difluorobenzo[d][1,3]dioxol-5-yl) cyclopropanecarboxamido)-3-methylpyridin-2-yl)benzoic acid.

In another embodiment, the additional agent is a nutritional agent. Exemplary such agents include pancrelipase (pancreating enzyme replacement), including Pancrease®, Pancreacarb®, Ultrase®, or Creon®, Liprotomase® (formerly Trizytek®), Aquadeks®, or glutathione inhalation. In one embodiment, the additional nutritional agent is pancrelipase.

In one embodiment, the additional agent is a CFTR modulator other than a compound of the present invention.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Form A described herein or a pharmaceutically acceptable composition thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to modulating CFTR activity in a biological sample or a patient (e.g., in vitro or in vivo), which method comprises administering to the patient, or contacting said biological sample with Form A described herein or a pharmaceutically acceptable composition thereof. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of CFTR in a biological sample is useful for a variety of purposes that are known to one of skill in the art. Examples of such purposes include, but are not limited to, the study of CFTR in biological and pathological phenomena; and the comparative evaluation of new modulators of CFTR.

In yet another embodiment, a method of modulating activity of an anion channel in vitro or in vivo, is provided comprising the step of contacting said channel with Form A described herein or a pharmaceutically acceptable composition thereof. In preferred embodiments, the anion channel is a chloride channel or a bicarbonate channel. In other preferred embodiments, the anion channel is a chloride channel.

According to an alternative embodiment, the present invention provides a method of increasing the number of functional CFTR in a membrane of a cell, comprising the step of contacting said cell with Form A described herein or a pharmaceutically acceptable composition thereof.

According to another preferred embodiment, the activity of the CFTR is measured by measuring the transmembrane voltage potential. Means for measuring the voltage potential across a membrane in the biological sample may employ any of the known methods in the art, such as optical membrane potential assay or other electrophysiological methods.

The optical membrane potential assay utilizes voltage-sensitive FRET sensors described by Gonzalez and Tsien (See J. E. and R. Y. Tsien (1995) "Voltage sensing by fluorescence resonance energy transfer in single cells." *Biophys J* 69(4): 1272-80, and Gonzalez, J. E. and R. Y. Tsien (1997); "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, $DiSBAC_2(3)$, and a fluorescent phospholipid, CC2-DMPE, which is attached to the outer leaflet of the plasma membrane and acts as a FRET donor. Changes in membrane potential ($V_m$) cause the negatively charged $DiSBAC_2(3)$ to redistribute across the plasma membrane and the amount of energy transfer from CC2-DMPE changes accordingly. The changes in fluorescence emission can be monitored using VIPR™ II, which is an integrated liquid handler and fluorescent detector designed to conduct cell-based screens in 96- or 384-well microtiter plates.

In another aspect the present invention provides a kit for use in measuring the activity of CFTR or a fragment thereof in a biological sample in vitro or in vivo comprising (i) a composition comprising Form A or any of the above embodiments; and (ii) instructions for a) contacting the composition with the biological sample and b) measuring activity of said CFTR or a fragment thereof. In one embodiment, the kit further comprises instructions for a) contacting an additional composition with the biological sample; b) measuring the activity of said CFTR or a fragment thereof in the presence of said additional compound, and c) comparing the activity of the CFTR in the presence of the additional compound with the density of the CFTR in the presence of Form A described herein. In preferred embodiments, the kit is used to measure the density of CFTR.

In order that the invention described herein may be more fully understood, the following examples are set forth. It should be understood that these examples are for illustrative purposes only and are not to be construed as limiting this invention in any manner.

EXAMPLES

Methods & Materials
XRPD (X-ray Powder Diffraction)
The X-ray powder diffraction (XRPD) data were recorded at room temperature using a Rigaku/MSC MiniFlex Desktop Powder X-ray Diffractometer (Rigaku, The Woodlands, Tex.). The X-Ray was generated using Cu tube operated at 30 kV and 15 mA with Kβ suppression filter. The divergence slit was variable with the scattering and receiving slits set at 4.2 degree and slit 0.3 mm, respectively. The scan mode was fixed time (FT) with 0.02 degree step width and count time of 2.0 seconds. The Powder X-ray Diffractometer was calibrated using reference standard: 75% Sodalite ($Na_3Al_4Si_4O_{12}Cl$) and 25% Silicon (Rigaku, Cat #2100/ALS). The six samples stage was used with zero background sample holders (SH-LBSI511-RNDB). The powder sample was placed on the indented area and flattened with glass slide.

FTIR (Fourier Transform Infrared) Spectroscopy
FTIR spectra were collected from a Thermo Scientific, Nicolet 6700 FT-IR spectrometer, with smart orbit sampling compartment, diamond window, using Software: Omnic, 7.4. The powder sample was placed directly on the diamond crystal and pressure was added to conform the surface of the sample to the surface of the diamond crystal. The background spectrum was collected and then the sample spectrum was collected. The collection settings were as follows:
Detector: DTGS KBr;
Beamsplitter: KBr;
Source: IR;
Scan range: 4000-400 $cm^{-1}$;
Gain: 8.0;
Optical velocity: 0.6329 cm/sec;
Aperture: 100;
No. of scans: 32; and
Resolution: 4 $cm^{-1}$.

Example 1

Preparation of 4-oxo-5-(trifluoromethyl)-1,4-dihydroquinoline-3-carboxylic acid (7)

2-Chloro-5-(trifluoromethyl)aniline 2 (200 g, 1.023 mol), diethyl 2-(ethoxymethylene)malonate 3 (276 g, 1.3 mol) and toluene (100 mL) were combined under a nitrogen atmosphere in a three-neck, 1-L round bottom flask equipped with Dean-Stark condenser. The solution was heated with stirring to 140° C. and the temperature was maintained for 4 h. The reaction mixture was cooled to 70° C. and hexane (600 mL) was slowly added. The resulting slurry was stirred and allowed to warm to room temperature. The solid was collected by filtration, washed with 10% ethyl acetate in hexane (2×400 mL) and then dried under vacuum to provide a white solid (350 g, 94% yield) as the desired condensation product diethyl 2-((2-chloro-5-(trifluoromethyl)phenylamino) methylene) malonate 4. $^1$H NMR (400 MHz, DMSO-$d_6$) δ 11.28 (d, J=13.0 Hz, 1H), 8.63 (d, J=13.0 Hz, 1H), 8.10 (s, 1H), 7.80 (d, J=8.3 Hz, 1H), 7.50 (dd, J=1.5, 8.4 Hz, 1H), 4.24 (q, J=7.1 Hz, 2H), 4.17 (q, J=7.1 Hz,2H),1.27 (m, 6H).

Preparation of ethyl 8-chloro-4-oxo-5-(trifluoromethyl)-1,4-dihydroquinoline-3-carboxylate (5). A 3-neck, 1-L flask was charged with Dowtherm® (200 mL, 8 mL/g), which was degassed at 200° C. for 1 h. The solvent was heated to 260° C. and charged in portions over 10 min with diethyl 2-((2-chloro-5-(trifluoromethyl)phenylamino) methylene)malonate 4 (25 g, 0.07 mol). The resulting mixture was stirred at 260° C. for 6.5 hours (h) and the resulting ethanol byproduct removed by distillation. The mixture was allowed to slowly cool to 80° C. Hexane (150 mL) was slowly added over 30 minutes (min), followed by an additional 200 mL of hexane added in one portion. The slurry was stirred until it had reached room temperature. The solid was filtered, washed with hexane (3 ×150 mL), and then dried under vacuum to provide ethyl 8-chloro-4-oxo-5-(trifluoromethyl)-1,4-dihydroquinoline-3-carboxylate 5 as a tan solid (13.9 g, 65% yield). ¹H NMR (400 MHz, DMSO-$d_6$) δ 11.91 (s, 1H), 8.39 (s, 1H), 8.06 (d, J=8.3 Hz, 1H), 7.81 (d, J=8.4 Hz, 1H), 4.24 (q, J=7.1 Hz, 2H), 1.29 (t, J=7.1 Hz, 3H).

Preparation of ethyl 4-oxo-5-(trifluoromethyl)-1H-quinoline-3-carboxylate (6). A 3-neck, 5-L flask was charged with of ethyl 8-chloro- 4-oxo-5-(trifluoromethyl)-1,4-dihydroquinoline-3-carboxylate 5 (100 g, 0.3 mol), ethanol (1250 mL, 12.5 mL/g) and triethylamine (220 mL, 1.6 mol). The vessel was then charged with 10 g of 10% Pd/C (50% wet) at 5° C. The reaction was stirred vigorously under hydrogen atmosphere for 20 h at 5° C., after which time the reaction mixture was concentrated to a volume of approximately 150 mL. The product, ethyl 4-oxo-5-(trifluoromethyl)-1H-quinoline-3-carboxylate 6, as a slurry with Pd/C, was taken directly into the next step.

Preparation of 4-oxo-5-(trifluoromethyl)-1,4-dihydroquinoline-3-carboxylic acid (7). Ethyl 4-oxo-5-(trifluoromethyl)-1H-quinoline-3-carboxylate 6 (58 g, 0.2 mol, crude reaction slurry containing Pd/C) was suspended in NaOH (814 mL of 5 M, 4.1 mol) in a 1-L flask with a reflux condenser and heated at 80° C. for 18 h, followed by further heating at 100° C. for 5 h. The reaction was filtered warm through packed Celite to remove Pd/C and the Celite was rinsed with 1 N NaOH. The filtrate was acidified to about pH 1 to obtain a thick, white precipitate. The precipitate was filtered then rinsed with water and cold acetonitrile. The solid was then dried under vacuum to provide 4-oxo-5-(trifluoromethyl)-1,4-dihydroquinoline-3-carboxylic acid 7 as a white solid (48 g, 92% yield). ¹H NMR (400.0 MHz, DMSO-$d_6$) δ 15.26 (s, 1H), 13.66 (s, 1H), 8.98 (s, 1H), 8.13 (dd, J=1.6, 7.8 Hz, 1H), 8.06-7.99 (m, 2H).

Example 2

Preparation of 4-(7-azabicyclo[2.2.1]heptan-7-yl)-2-(trifluoromethyl)aniline

Preparation of 7-[4-nitro-3-(trifluoromethyl)phenyl]-7-azabicyclo[2.2.1]heptane (20). To a flask containing 7-azabicyclo[2.2.1]heptane hydrochloride 9 (4.6 g, 34.43 mmol, obtained from under a nitrogen atmosphere was added a solution of 4-fluoro-1-nitro-2-(trifluoromethyl)benzene 8 (6.0 g, 28.69 mmol) and triethylamine (8.7 g, 12.00 mL, 86.07 mmol) in acetonitrile (50 mL). The reaction flask was heated at 80° C. under a nitrogen atmosphere for 16 h. The reaction mixture was allowed to cool and then was partitioned between water and dichloromethane. The organic layer was washed with 1 M HCl, dried over $Na_2SO_4$, filtered, and concentrated to dryness. Purification by silica gel chromatography (0-10% ethyl acetate in hexanes) yielded 7-[4-nitro-3-(trifluoromethyl)phenyl]-7-azabicyclo[2.2.1]heptane 10 (7.2 g, 88% yield) as a yellow solid. ¹H NMR (400.0 MHz, DMSO-$d_6$) δ 8.03 (d, J=9.1 Hz, 1H), 7.31 (d, J=2.4 Hz, 1H), 7.25 (dd, J=2.6, 9.1 Hz, 1H), 4.59 (s, 2H), 1.69-1.67 (m, 4H), 1.50 (d, J=7.0 Hz, 4H).

Preparation of 4-(7-azabicyclo[2.2.1]heptan-7-yl)-2-(trifluoromethyl)aniline (11). A flask charged with 7-[4-nitro-3-(trifluoromethyl)phenyl]-7-azabicyclo[2.2.1]heptane 10 (7.07 g, 24.70 mmol) and 10% Pd/C (0.71 g, 6.64 mmol) was evacuated and then flushed with nitrogen. Ethanol (22 mL) was added and the reaction flask was fitted with a hydrogen balloon. After stirring vigorously for 12 h, the reaction mixture was purged with nitrogen and Pd/C was removed by filtration. The filtrate was concentrated to a dark oil under reduced pressure and the residue purified by silica gel chromatography (0-15% ethyl acetate in hexanes) to provide 4-(7-azabicyclo[2.2.1]heptan-7-yl)-2-(trifluoromethyl)aniline 11 as a purple solid (5.76 g, 91% yield).

¹H NMR (400.0 MHz, DMSO-$d_6$) δ 6.95 (dd, J=2.3, 8.8 Hz, 1H), 6.79 (d, J=2.6 Hz, 1H), 6.72 (d, J=8.8 Hz, 1H), 4.89 (s, 2H), 4.09 (s, 2H), 1.61-1.59 (m, 4H) and 1.35 (d, J=6.8 Hz, 4H).

Example 3

Preparation of N-(4-(7-azabicyclo[2.2.1]heptan-7-yl)-2-(trifluoromethyl)phenyl)-4-oxo-5-(trifluoromethyl)-1,4-dihydroquinoline-3-carboxamide (Compound 1)

Compound 1

To a solution of 4-oxo-5-(trifluoromethyl)-1H-quinoline-3-carboxylic acid 7 (9.1 g, 35.39 mmol) and 4-(7-azabicyclo[2.2.1]heptan-7-yl)-2-(trifluoromethyl)aniline 11 (9.2 g, 35.74 mmol) in 2-methyltetrahydrofuran (91.00 mL) was added propyl phosphonic acid cyclic anhydride (50% solution in ethyl acetate, 52.68 mL, 88.48 mmol) and pyridine (5.6 g, 5.73 mL, 70.78 mmol) at room temperature. The reaction flask heated at 65° C. for 10 h under a nitrogen atmosphere. After cooling to room temperature the reaction was then diluted with ethyl acetate and quenched with saturated $Na_2CO_3$ solution (50 mL). The layers were separated, and the aqueous layer was extracted twice more with ethyl acetate. The combined organic layers were washed with water, dried over $Na_2SO_4$, filtered and concentrated to a tan solid. The crude solid product was slurried in ethyl acetate/diethyl ether (2:1), collected by vacuum filtration, and washed twice more with ethyl acetate/diethyl ether (2:1) to provide the product as a light yellow crystalline powder. The powder was dissolved in warm ethyl acetate and absorbed onto Celite. Purification by silica gel chromatography (0-50% ethyl acetate in dichloromethane) provided N-(4-(7-azabicyclo[2.2.1]heptan-7-yl)-2-(trifluoromethyl)phenyl)-4-oxo-5-(trifluoromethyl-1,4-dihydroquinoline-3-carboxamide (Compound 1) as a white crystalline solid (Form A) (13.5 g, 76% yield). LC/MS m/z 496.0 [M+H]$^+$, retention time 1.48 mm (RP-$C_{18}$, 10-99% $CH_3CN$/0.05% TFA over 3 min). $^1$H NMR (400.0 MHz, DMSO-$d_6$) δ 13.08 (s, 1H), 12.16 (s, 1H), 8.88 (s, 1H), 8.04 (dd, J=2.1, 7.4 Hz, 1H), 7.95-7.88 (m. 3H), 7.22 (dd. 2.5. 8.9 Hz, 1H), 7.16 (d, J=2.5 Hz, 1H), 4.33 (s, 2H), 1.67 (d, J=6.9 Hz, 4H), 1.44 (d, J=6.9 Hz, 4H).

The powder diffractogram of Form A is shown in FIG. 1.

Table 1, below provides representative XRPD peaks of Form A.

TABLE 1

| Form A XRPD Peaks | |
|---|---|
| 2 Theta (degrees) | Intensity (%) |
| 7.90 | 100.0 |
| 9.28 | 10.8 |
| 11.90 | 12.8 |

TABLE 1-continued

| Form A XRPD Peaks | |
|---|---|
| 2 Theta (degrees) | Intensity (%) |
| 14.38 | 35.2 |
| 15.08 | 12.6 |
| 15.80 | 34.1 |
| 16.96 | 25.2 |
| 17.66 | 13.8 |
| 19.28 | 39.4 |
| 20.06 | 20.2 |
| 21.36 | 14.5 |
| 21.80 | 94.2 |
| 23.40 | 30.0 |
| 23.80 | 92.0 |
| 25.64 | 8.9 |
| 26.82 | 6.4 |
| 29.36 | 8.1 |
| 29.72 | 18.1 |
| 30.14 | 14.2 |
| 31.20 | 9.9 |

Figure 2:
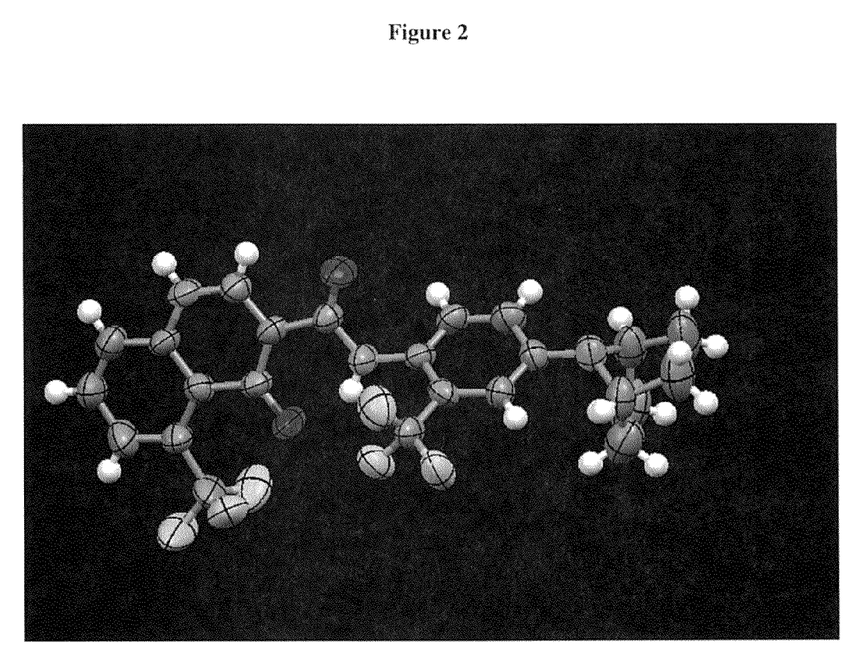
FIG. 2 is a conformational picture of Form A based on single X-ray crystal analysis.

Conformational pictures of Form A based on single crystal X-ray analysis are shown in FIG. 2. Diffraction data were acquired on a Bruker Apex II Diffractometer equipped with sealed tube CuK-alpha source and an Apex II CCD detector. The structure was solved and refined using SHELX program (Sheldrick, G. M., Acta Cryst. A64, pp. 112-122 (2008)). Based on intensities, statistics and symmetry, the structure was solved and refined in a trigonal crystal system and an R-3 space group. Form A has the following unit cell dimensions: a=19.1670(4) Å, b=19.1670(4) Å, c=33.6572(12) Å, α=90°, β=90°, and γ=120°.

Figure 3:
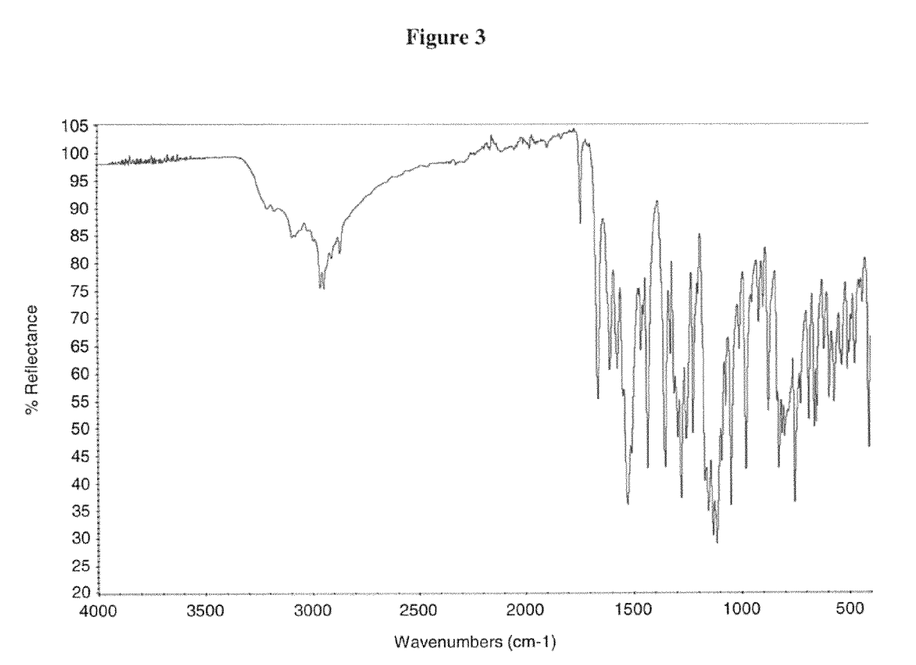
FIG. 3 provides an FTIR spectrum of Form A.

An FTIR spectra of From A is provided in FIG. 3.

Table 2, below provides representative FTIR peaks of Form A.

TABLE 2

| Form A FTIR Peaks | |
|---|---|
| Position (cm$^{-1}$) | Intensity |
| 407.4 | 46.07 |
| 436.7 | 72.55 |
| 471.5 | 61.17 |
| 497.8 | 63.61 |
| 505.7 | 60.34 |
| 532.9 | 61.14 |
| 567.8 | 54.31 |
| 590.7 | 55.23 |
| 614.4 | 64.01 |
| 649.7 | 50.74 |
| 661.0 | 49.82 |
| 686.8 | 51.43 |
| 726.1 | 53.80 |
| 751.4 | 35.60 |
| 798.1 | 48.21 |
| 808.8 | 48.47 |
| 824.8 | 42.25 |
| 875.5 | 52.89 |
| 898.6 | 71.77 |
| 918.7 | 68.93 |
| 977.7 | 42.31 |
| 1008.1 | 64.09 |
| 1047.3 | 35.70 |
| 1072.5 | 53.76 |
| 1091.2 | 43.79 |
| 1113.4 | 28.46 |
| 1131.4 | 30.00 |
| 1153.0 | 34.61 |
| 1168.3 | 40.13 |
| 1199.3 | 74.26 |
| 1221.8 | 48.07 |
| 1253.1 | 47.84 |

TABLE 2-continued

Form A FTIR Peaks

| Position (cm$^{-1}$) | Intensity |
|---|---|
| 1277.6 | 36.67 |
| 1291.7 | 48.07 |
| 1310.8 | 55.99 |
| 1329.1 | 63.21 |
| 1352.8 | 42.30 |
| 1433.2 | 42.45 |
| 1463.0 | 63.68 |
| 1526.0 | 35.86 |
| 1574.0 | 60.60 |
| 1607.5 | 60.30 |
| 1662.6 | 55.12 |
| 1740.9 | 86.74 |
| 2870.0 | 81.63 |
| 2947.7 | 75.12 |
| 2963.8 | 75.30 |
| 3092.7 | 84.58 |

Assays for Detecting and Measuring ΔF508-CFTR Potentiation Properties of Compounds Membrane Potential Optical Methods for Assaying ΔF508-CFTR Modulation Properties of Compounds The assay utilizes fluorescent voltage sensing dyes to measure changes in membrane potential using a fluorescent plate reader (e.g., FLIPR III, Molecular Devices, Inc.) as a readout for increase in functional ΔF508-CFTR in NIH 3T3 cells. The driving force for the response is the creation of a chloride ion gradient in conjunction with channel activation by a single liquid addition step after the cells have previously been treated with compounds and subsequently loaded with a voltage sensing dye.

Identification of Potentiator Compounds

To identify potentiators of ΔF508-CFTR, a double-addition HTS assay format was developed. This HTS assay utilizes fluorescent voltage sensing dyes to measure changes in membrane potential on the FLIPR III as a measurement for increase in gating (conductance) of ΔF508 CFTR in temperature-corrected ΔF508 CFTR NIH 3T3 cells. The driving force for the response is a Cl_ ion gradient in conjunction with channel activation with forskolin in a single liquid addition step using a fluoresecent plate reader such as FLIPR III after the cells have previously been treated with potentiator compounds (or DMSO vehicle control) and subsequently loaded with a redistribution dye.

Solutions

Bath Solution #1: (in mM) NaCl 160, KCl 4.5, CaCl$_2$ 2, MgCl$_2$ 1, HEPES 10, pH 7.4 with NaOH.

Chloride-free bath solution: chloride salts in bath solution #1 are substituted with gluconate salts.

Cell Culture

NIH3T3 mouse fibroblasts stably expressing ΔF508-CHR are used for optical measurements of membrane potential. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1×pen/strep, and 25 mM HEPES in 175 cm$^2$ culture flasks. For all optical assays, the cells were seeded at ~20,000/well in 384-well matrigel-coated plates and cultured for 2 hrs at 37° C. before culturing at 27° C. for 24 hrs. for the potentiator assay. For the correction assays, the cells are cultured at 27° C. or 37° C. with and without compounds for 16-24 hours. Electrophysiological Assays for assaying ΔF508-CFTR modulation properties of compounds.

Using Chamber Assay

Using chamber experiments were performed on polarized airway epithelial cells expressing ΔF508-CFTR to further characterize the ΔF508-CFTR modulators identified in the optical assays. Non-CF and CF airway epithelia were isolated from bronchial tissue, cultured as previously described (Galietta, L. J. V., Lantero, S., Gazzolo, A., Sacco, O., Romano, L., Rossi, G. A., & Zegarra-Moran, O. (1998) In Vitro Cell. Dev. Biol. 34,478-481), and plated onto Costar® Snapwell™ filters that were precoated with NIH3T3-conditioned media. After four days the apical media was removed and the cells were grown at an air liquid interface for >14 days prior to use. This resulted in a monolayer of fully differentiated columnar cells that were ciliated, features that are characteristic of airway epithelia. Non-CF HBE were isolated from non-smokers that did not have any known lung disease. CF-HBE were isolated from patients homozygous for ΔF508-CFTR.

HBE grown on Costar® Snapwell™ cell culture inserts were mounted in an Ussing chamber (Physiologic Instruments, Inc., San Diego, Calif.), and the transepithelial resistance and short-circuit current in the presence of a basolateral to apical Cl$^-$ gradient ($I_{SC}$) were measured using a voltage-clamp system (Department of Bioengineering, University of Iowa, IA). Briefly, HBE were examined under voltage-clamp recording conditions ($V_{hold}$=0 mV) at 37° C. The basolateral solution contained (in mM) 145 NaCl, 0.83 K$_2$HPO$_4$, 3.3 KH$_2$PO$_4$, 1.2 MgCl$_2$, 1.2 CaCl$_2$, 10 Glucose, 10 HEPES (pH adjusted to 7.35 with NaOH) and the apical solution contained (in mM) 145 NaGluconate, 1.2 MgCl$_2$, 1.2 CaCl$_2$, 10 glucose, 10 HEPES (pH adjusted to 7.35 with NaOH).

Identification of Potentiator Compounds

Typical protocol utilized a basolateral to apical membrane Cl$^-$ concentration gradient. To set up this gradient, normal ringers was used on the basolateral membrane, whereas apical NaCl was replaced by equimolar sodium gluconate (titrated to pH 7.4 with NaOH) to give a large Cl$^-$ concentration gradient across the epithelium. Forskolin (10 μM) and all test compounds were added to the apical side of the cell culture inserts. The efficacy of the putative ΔF508-CFTR potentiators was compared to that of the known potentiator, genistein.

Patch-clamp Recordings

Total Cl$^-$ current in ΔF508-NIH3T3 cells was monitored using the perforated-patch recording configuration as previously described (Rae, J., Cooper, K., Gates, P., & Watsky, M. (1991) J. Neurosci. Methods 37, 15-26). Voltage-clamp recordings were performed at 22° C. using an Axopatch 200B patch-clamp amplifier (Axon Instruments Inc., Foster City, Calif.). The pipette solution contained (in mM) 150 N-methyl-D-glucamine (NMDG)-Cl, 2 MgCl$_2$, 2 CaCl$_2$, 10 EGTA, 10 HEPES, and 240 pg/ml amphotericin-B (pH adjusted to 7.35 with HCl). The extracellular medium contained (in mM) 150 NMDG-Cl, 2 MgCl$_2$, 2 CaCl$_2$, 10 HEPES (pH adjusted to 7.35 with HCl). Pulse generation, data acquisition, and analysis were performed using a PC equipped with a Digidata 1320 A/D interface in conjunction with Clampex 8 (Axon Instruments Inc.). To activate ΔF508-CFTR, 10 μM forskolin and 20 μM genistein were added to the bath and the current-voltage relation was monitored every 30 sec.

Identification of Potentiator Compounds

The ability of ΔF508-CFTR potentiators to increase the macroscopic ΔF508-CFTR Cl$^-$ current ($I_{\Delta F508}$) in NIH3T3 cells stably expressing ΔF508-CFTR was also investigated using perforated-patch-recording techniques. The potentiators identified from the optical assays evoked a dose-dependent increase in $I\Delta_{F508}$ with similar potency and efficacy observed in the optical assays. In all cells examined, the reversal potential before and during potentiator application was around −30 mV, which is the calculated $E_{Cl}$ (−28 mV).

Cell Culture

NIH3T3 mouse fibroblasts stably expressing ΔF508-CFTR are used for whole-cell recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME,1×pen/strep, and 25 mM HEPES in 175 cm² culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

Single-channel Recordings

Gating activity of wt-CFTR and temperature-corrected ΔF508-CFTR expressed in NIH3T3 cells was observed using excised inside-out membrane patch recordings as previously described (Dalemans, W., Barbry, P., Champigny, G., Jallat, S., Dott, K., Dreyer, D., Crystal, R. G., Pavirani, A., Lecocq, J-P., Lazdunski, M. (1991) *Nature* 354, 526-528) using an Axopatch 200B patch-clamp amplifier (Axon Instruments Inc.). The pipette contained (in mM): 150 NMDG, 150 aspartic acid, 5 $CaCl_2$, 2 $MgCl_2$, and 10 HEPES (pH adjusted to 7.35 with Tris base). The bath contained (in mM): 150 NMDG-Cl, 2 $MgCl_2$, 5 EGTA, 10 TES, and 14 Tris base (pH adjusted to 7.35 with HCl). After excision, both wt- and ΔF508-CFTR were activated by adding 1 mM Mg-ATP, 75 nM of the catalytic subunit of cAMP-dependent protein kinase (PKA; Promega Corp. Madison, Wis.), and 10 mM NaF to inhibit protein phosphatases, which prevented current rundown. The pipette potential was maintained at 80 mV. Channel activity was analyzed from membrane patches containing ≦2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

Cell Culture

NIH3T3 mouse fibroblasts stably expressing ΔF508-CFTR are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1×pen/strep, and 25 mM HEPES in 175 cm² culture flasks. For single channel recordings, 2,500-5,000 cells were seeded on poly-L-lysine-coated glass coverslips and cultured for 24-48 hrs at 27° C. before use.

Compound 1 Form A is useful as a modulator of ATP binding cassette transporters. The $EC_{50}$ (μm) of Compound 1 Form A was measured to be less than 2.0 μM. The efficacy of Compound 1 Form A was calculated to be from 100% to 25%. It should be noted that 100% efficacy is the maximum response obtained with 4-methyl-2-(5-phenyl-1H-pyrazol-3-yl)phenol.

What is claimed is:

1. A Crystalline N-(4-(7-azabicyclo[2.2.1]heptan-7-yl)-2-(trifluoromethyl)phenyl)-4-oxo-5-(trifluoromethyl)-1,4-dihydroquinoline-3-carboxamide characterized as Form A, wherein the Form A is characterized by a peak at about 7.9 degrees, and a peak at about 11.9 degrees in an X-ray powder diffraction pattern.

2. Form A of claim 1, wherein the Form A is further characterized by a peak at about 9.3 degrees in an X-ray powder diffraction pattern.

3. Form A of claim 1, wherein the Form A is further characterized by a peak at about 14.4 degrees in an X-ray powder diffraction pattern.

4. Form A of claim 3, wherein the Form A is further characterized by a peak at about 15.8 degrees in an X-ray powder diffraction pattern.

5. Form A of claim 1, wherein the Form A is further characterized by a peak at about 19.3 degrees in an X-ray powder diffraction pattern.

6. Form A of claim 4, wherein the Form A is further characterized by a peak at about 21.8 degrees in an X-ray powder diffraction pattern.

7. Form A of claim 6, wherein the Form A is further characterized by a peak at about 23.8 degrees in an X-ray powder diffraction pattern.

8. Form A of claim 1, wherein the Form A is further characterized by a peak at about 14.4 degrees, and a peak at about 15.8 degrees in an X-ray powder diffraction pattern.

9. Form A of claim 1, wherein the Form A is further characterized by a diffraction pattern shown to that of FIG. 1.

10. Form A of claim 8, wherein the Form A is characterized by a peak at about 9.3 degrees, a peak at about 19.3 degrees, a peak at about 21.8 degrees and a peak at about 23.8 degrees.

11. Form A of claim 7, wherein the Form A is further characterized by a peak at about 15.1 degrees in an X-ray powder diffraction pattern, a peak at about 17.0 degrees in an X-ray powder diffraction pattern, a peak at about 17.7 degrees in an X-ray powder diffraction pattern, a peak at about 21.4 degrees in an X-ray powder diffraction pattern, a peak at about 23.4 degrees in an X-ray powder diffraction pattern.

12. Form A of claim 11, wherein the Form A is further characterized by a peak at about 25.6 degrees, a peak at about 26.8 degrees, a peak at about 29.4 degrees, a peak at about 29.7 degrees, a peak at about 30.1 degrees and a peak at about 31.2 degrees in an X-ray powder diffraction pattern.

13. Form A of claim 7, wherein the Form A is further characterized by a peak at about 25.6 degrees, a peak at about 26.8 degrees, a peak at about 29.4 degrees, a peak at about 29.7 degrees, a peak at about 30.1 degrees and a peak at about 31.2 degrees in an X-ray powder diffraction pattern.

* * * * *